US010674967B2

(12) United States Patent
Rahman et al.

(10) Patent No.: US 10,674,967 B2
(45) Date of Patent: Jun. 9, 2020

(54) ESTIMATING BODY COMPOSITION ON A MOBILE DEVICE

(71) Applicant: Samsung Electronics Co., Ltd., Suwon-si (KR)

(72) Inventors: Mahbubur Rahman, Sunnyvale, CA (US); Jilong Kuang, San Jose, CA (US); Daniyal Liaqat, Toronto (CA); Jun Gao, Menlo Park, CA (US); Nasson Boroumand, Gold River, CA (US)

(73) Assignee: Samsung Electronics Co., Ltd., Suwon-si (KR)

( * ) Notice: Subject to any disclaimer, the term of this patent is extended or adjusted under 35 U.S.C. 154(b) by 155 days.

(21) Appl. No.: 15/888,883

(22) Filed: Feb. 5, 2018

(65) Prior Publication Data

US 2019/0239820 A1    Aug. 8, 2019

(51) Int. Cl.
| | | |
|---|---|---|
| *A61B 5/00* | (2006.01) | |
| *A61B 5/05* | (2006.01) | |
| *A61B 5/053* | (2006.01) | |
| *A61B 5/087* | (2006.01) | |
| *A61B 5/145* | (2006.01) | |
| *A61B 7/04* | (2006.01) | |

(52) U.S. Cl.
CPC .......... *A61B 5/7278* (2013.01); *A61B 5/0004* (2013.01); *A61B 5/0507* (2013.01); *A61B 5/0537* (2013.01); *A61B 5/087* (2013.01); *A61B 5/14542* (2013.01); *A61B 7/04* (2013.01)

(58) Field of Classification Search
CPC .. A61B 7/04; A61B 5/087; A61B 5/08; A61B 5/083; A61B 5/0833; A61B 5/0836; A61B 5/0871; A61B 5/0873; A61B 5/0875; A61B 5/0876; A61B 5/0878; A61B 5/09; A61B 5/091; A61B 5/0537; A61B 7/003
See application file for complete search history.

(56) References Cited

U.S. PATENT DOCUMENTS

| | | |
|---|---|---|
| 8,485,982 B2 | 7/2013 | Gavish et al. |
| 9,723,997 B1 | 8/2017 | Lamego |
| 2004/0186390 A1 | 9/2004 | Ross et al. |

(Continued)

FOREIGN PATENT DOCUMENTS

| | | |
|---|---|---|
| EP | 1754442 A2 | 2/2007 |
| JP | 2006192255 A | 7/2006 |

(Continued)

OTHER PUBLICATIONS

International Search Report dated Oct. 24, 2018 in connection with International Patent Application No. PCT/KR2018/008352, 3 pages.

(Continued)

*Primary Examiner* — Michael W Kahelin

(57) ABSTRACT

A method, electronic device, and non-transitory computer readable medium for estimating body composition are provided. The method includes receiving a set of forced breath data from an electronic device. The method also includes deriving a flow rate based on the set of forced breath data. The method further includes determining a body composition based on the derived flow rate of the set of forced breath data.

20 Claims, 8 Drawing Sheets

(56) References Cited

U.S. PATENT DOCUMENTS

| | | | |
|---|---|---|---|
| 2007/0043302 A1* | 2/2007 | Masuo | A61B 5/0537 600/547 |
| 2010/0121216 A1 | 5/2010 | Hamaguchi et al. | |
| 2011/0046895 A1 | 2/2011 | Moerman | |
| 2011/0125060 A1* | 5/2011 | Telfort | A61B 7/003 600/586 |
| 2013/0310636 A1 | 11/2013 | Krans et al. | |
| 2013/0331662 A1 | 12/2013 | Stoian et al. | |
| 2018/0140252 A1* | 5/2018 | Luxon | A61B 5/0456 |

FOREIGN PATENT DOCUMENTS

| | | |
|---|---|---|
| JP | 3872889 B2 | 1/2007 |
| WO | 2006/112733 A1 | 10/2006 |
| WO | 2013/185041 A1 | 12/2013 |

OTHER PUBLICATIONS

Written Opinion of the International Searching Authority dated Oct. 24, 2018 in connection with International Patent Application No. PCT/KR2018/008352, 6 pages.

"High-end and Non-contact Sensor Technology for Respiration Monitoring", XeThru White Paper, Novelda AS, Dec. 2014, 11 pages.

Costa, "Analysis of Pulmonary Airflow on a Smartphone Application", Dissertation, Integrated Master's Degree in Bioengineering, Biomedical Engineering Branch, Faculdade de Engenharia da Universidade do Porto, Jun. 2016, 65 pages.

Larson et al., "SpiroSmart: Using a Microphone to Measure Lung Function on a Mobile Phone", Proceedings of the 2012 ACM Conference on Ubiquitous Computing (UbiComp'12), Sep. 2012, pp. 280-289.

Larson et al., "Tracking Lung Function on any Phone", Proceedings of the 3rd ACM Symposium on Computing for Development (ACM DEV '13), Article 29, Jan. 2013, 2 pages.

Xu et al., "mCOPD: Mobile Phone Based Lung Function Diagnosis and Exercise System for COPD", Proceedings of the 6th International Conference on Pervasive Technologies Related to Assistive Environments (PETRA '13), Article 45, May 2013, 8 pages.

Farina et al., "A Smartphone Application for Personal Assessments of Body Composition and Phenotyping", Sensors, vol. 16, No. 12, 2163, Dec. 2016, 9 pages.

Goel et al., "SpiroCall: Measuring Lung Function over a Phone Call", Proceedings of the 2016 CHI Conference on Human Factors in Computing Systems (CHI '16), May 2016, pp. 5675-5685.

Comstock, "Newly granted Apple patent shows ways to turn an iPhone into a health sensor", MobiHealthNews, Aug. 14, 2017, 2 pages. http://www.mobihealthnews.com/content/newly-granted-apple-patent-shows-ways-turn-iphone-health-sensor.

Costa et al., "The Impact of Obesity on Pulmonary Function in Adult Women", Clinics, vol. 63, No. 6, Dec. 2008, pp. 719-724.

"Weight Loss and Weight Management Market by Equipment (Fitness (Treadmill, Elliptical, Stair Stepper), Surgical Equipment (Biliopancreatic Diversion, Gastric Bypass)), Diet (Meal, Beverage, Supplement), and Weight Loss Services—Global Forecast to 2022", MarketsandMarkets Research Private Ltd., Report Code MD 5665, Oct. 2017, 2 pages. https://www.marketsandmarkets.com/Market-Reports/weight-loss-obesity-management-market-1152.html.

"Body Fat Calipers, MyoTape Body Tape Measure, and More Great Fitness Products!", AccuFitness, LLC., copyright 1999-2017, 4 pages. https://www.accumeasurefitness.com/.

Lawrenson, "Flow to Measure Your Body Fat % Using Calipers", Muscle & Strength LLC, copyright 2005-2017, 18 pages. https://www.muscleandstrength.com/tools/measure-bodyfat.

* cited by examiner

ESTIMATING BODY COMPOSITION ON A MOBILE DEVICE

TECHNICAL FIELD

Embodiments of this disclosure relate generally to determining body composition. More specifically, various embodiments of this disclosure relate to measuring lung function through pulmonary function tests to determine body composition using forced breathing techniques.

BACKGROUND

Weight alone is not a clear indicator of good health as weight does not distinguish between mass from body fat and mass from muscles. Therefore, weight of a person is not regarded as the sole test to determine the overall health of the person, as a person's weight often cannot indicate whether an individual is physically fit as compared to an individual that is overweight. A medical condition called obesity is a condition in which an individual has too much fat that puts the individual at risk for many serious medical conditions.

There is strong evidence linking cardiovascular disease, diabetes, certain forms of cancer, and many other diseases to obesity. Obesity partially contributes to about half of the chronic diseases. Weight alone is not a clear indicator of whether a person is obese. Common methods in health management concerning detecting obesity are based on measuring the weight of a person as well as inspecting the figure of the person as. Abdominal size or weight or both are widely used as an index for evaluating the figure and physique of a person. For example, if a person A and a person B were of the same height, if person A weights more than person B, then in certain instances, person A would have a higher degree of obesity than person B.

Body composition analysis plays an essential role in identifying someone as obese. Body composition includes identifying muscle mass, bone mass, organ mass, body fat mass, and the like. Analyzing a person's body composition often provides evidence as to the level of physical fitness of a person as well as whether a person suffers obesity. The ability to detect obesity can potentially help the person avoid lifestyle-related diseases so as to maintain good health.

SUMMARY

Embodiments of this disclosure provide a system and method for estimating body composition on a mobile device.

In a first embodiment, a method for determining body composition is provided. The method includes receiving a set of forced breath data from an electronic device. The method also includes deriving a flow rate based on the set of forced breath data. The method further includes determining a body composition based on the derived flow rate of the set of forced breath data.

In a second embodiment, an electronic device is provided. The electronic device includes at least one processor coupled to the communication interface and the memory. The at least one processor is configured to receive a set of forced breath data from an electronic device. The at least one processor is also configured to derive a flow rate based on the set of forced breath data. The at least one processor is further configured to determine determining a body composition based on the derived flow rate of the set of forced breath data.

In a third embodiment a non-transitory computer readable medium embodying a computer program is provided. The computer program includes program code that, when executed by at least one processor, causes the processor to receive a set of forced breath data from an electronic device; derive a flow rate based on the set of forced breath data; and determine determining a body composition based on the derived flow rate of the set of forced breath data.

Other technical features may be readily apparent to one skilled in the art from the following figures, descriptions, and claims.

Before undertaking the DETAILED DESCRIPTION below, it may be advantageous to set forth definitions of certain words and phrases used throughout this patent document. The term "couple" and its derivatives refer to any direct or indirect communication between two or more elements, whether or not those elements are in physical contact with one another. The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrase "associated with," as well as derivatives thereof, means to include, be included within, interconnect with, contain, be contained within, connect to or with, couple to or with, be communicable with, cooperate with, interleave, juxtapose, be proximate to, be bound to or with, have, have a property of, have a relationship to or with, or the like. The term "controller" means any device, system or part thereof that controls at least one operation. Such a controller may be implemented in hardware or a combination of hardware and software and/or firmware. The functionality associated with any particular controller may be centralized or distributed, whether locally or remotely. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Definitions for other certain words and phrases are provided throughout this patent document. Those of ordinary skill in the art should understand that in many if not most instances, such definitions apply to prior as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

Figure 1:
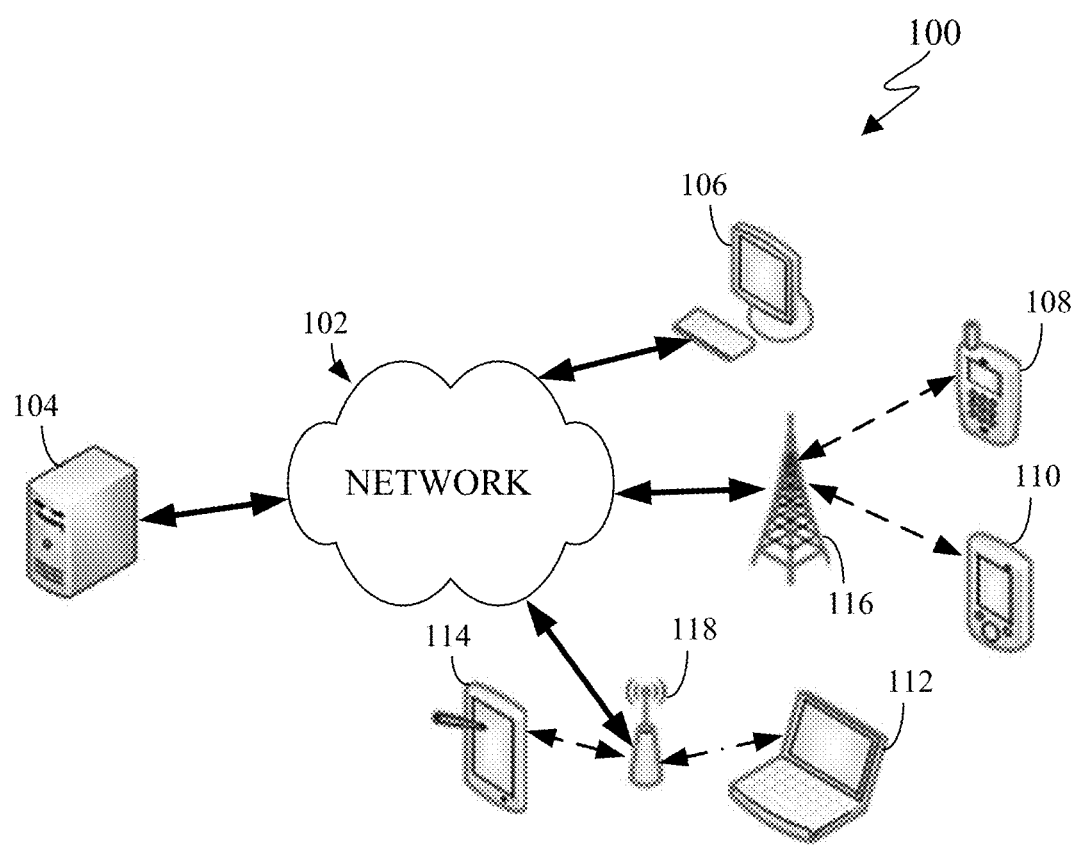
FIG. 1 illustrates an example communication system in accordance with embodiments of the present disclosure.

FIGS. 1 through 7, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably-arranged wireless communication system or device.

According to embodiments of the present disclosure, various methods for determining body composition are provided. Body composition is used to describe the percentages of fat, bone, water, and muscle within a person. Two persons of the same gender, height, and weight can look completely different based on differing body compositions. For example, muscular tissue is denser and takes up less space in a body than fatty tissue.

Measuring the weight of a person does not represent the entire picture of the body composition of the person. For example, body composition of a person includes determining the amount of visceral fat in a person. Visceral fat is the fat that accumulates around the internal organs of the abdominal area of a person. Accumulation of visceral fat is known to lead a number of diseases such as diabetes, high blood pressure, and a variety of cardiac diseases. Visceral fat is a significantly more important parameter to track than simply measuring the weight of a person. For this reason, deriving an amount of visceral fat on a person can potentially help the individual avoid lifestyle-related diseases and maintain good health.

Common methods of measuring the amount of visceral fat a person often require a clinical setting. For example, visceral fat can be measured using a skinfold caliper and various imaging devices such as a magnetic resonance imaging (MRI), X-ray. A skinfold caliper approximates the amount of visceral fat based on measuring by a caliper the amount of fat through the skin of a person at multiple locations. Such techniques are often expensive, mildly invasive, and uncomfortable to the patient being tested.

According to embodiments of the present disclosure, a direct relationship exists between obesity due to visceral fat and pulmonary functions. Specifically, estimating the body composition of a person can be captured based on breathing parameters similar to those used during a spirometry test. For example, as visceral fat accumulates around the organs of the abdominal area of a person, the lung capacity of a person is diminished due to the increase of the visceral fat. By capturing various forced breathing parameters that are associated with the pulmonary function of a user, a quantity of visceral fat that the particular person has can be determined. By determining the quantity of visceral fat of a person, a body composition analysis can be accomplished.

Spirometry is a medical test to assess the functioning and workings of the lungs of a person. For example, spirometry measures the lung function of a person and is often a central to the diagnosis and management of chronic lung disease such as asthma, chronic obstructive pulmonary disease (COPD), cystic fibrosis, and so forth. Spirometry measures the amount of air inhaled and exhaled and the time it takes a person to exhale. During a spirometry test an individual forcefully exhales through a flow monitoring device that measures the instantaneous flow and cumulative exhaled volume. The forceful exhalation is referred to as a forced breathing.

According to embodiments of the present disclosure, forced breathing is utilized to determine the body composition of a user. Forced breathing is utilized to determine the body composition of a user when the user inhales to fill their lungs, and then quickly exhales the entire volume. If the user has visceral fat that is accumulated around the abdominal organs, the visceral fat creates obstructions and impedes the person from performing to the forced breathing exercise to their full ability.

Embodiments of the present disclosure provide for situations in which an electronic device, such as mobile device, can function as a spirometer and calculate the body composition based on a variety of captured parameters. In certain embodiments, a phone is used to capture the forced breath through the phones microphone. Additional information can be provided such as the blood oxygenation level of the user through a blood oxygen saturation level (SpO2) sensor, user profile data to name a few.

FIG. 1 illustrates an example system 100 according to this disclosure. The embodiment of the system 100 shown in FIG. 1 is for illustration only. Other embodiments of the system 100 could be used without departing from the scope of this disclosure.

The system 100 includes network 102 that facilitates communication between various components in the system 100. For example, network 102 can communicate Internet Protocol (IP) packets, frame relay frames, Asynchronous Transfer Mode (ATM) cells, or other information between network addresses. The network 102 includes one or more local area networks (LANs), metropolitan area networks (MANs), wide area networks (WANs), all or a portion of a global network such as the Internet, or any other communication system or systems at one or more locations.

The network 102 facilitates communications between various server(s) 104 and various client devices 106-114. Server 104 can represent one or more servers. Each server 104 includes any suitable computing or processing device that can provide computing services for one or more client devices. Each server 104 could, for example, include one or more processing devices, one or more memories storing instructions and data, and one or more network interfaces facilitating communication over the network 102.

Each client device 106-114 represents any suitable computing or processing device that interacts with at least one server or other computing device(s) over the network 102. In this example, the client devices 106-114 include a desktop computer 106, a mobile telephone or mobile devices 108 (such as a smartphone), a personal digital assistant (PDA) 110, a laptop computer 112, and a tablet computer 114. However, any other or additional client devices could be used in the system 100.

In this example, some client devices 108-114 communicate indirectly with the network 102. For example, the client devices 108 and 110 (mobile devices 108 and PDA 110, respectively) communicate via one or more base stations 116, such as cellular base stations or eNodeBs (eNBs). Mobile devices 108 includes both smart phones and feature phones. Smart phones represent a class of mobile devices 108 that are a handheld device with a mobile operating system and an integrated mobile broadband cellular network connection for voice, short message service (SMS), and internet data communication. Feature phones represent a class of mobile devices 108 that are a midway point between a basic phone and a smart phone. Feature phones generally have voice calling and text messaging functions in addition to basic multimedia and internet capabilities. Also, the client devices 112 and 114 (laptop computer and tablet computer, respectively) communicate via one or more wireless access points 118, such as IEEE 802.11 wireless access points. Note that these are for illustration only and that each client device 106-114 could communicate directly with the network 102 or indirectly with the network 102 via any suitable intermediate device(s) or network(s).

In certain embodiments, the mobile device 108 (or any other client device 106-114) can transmit information securely and efficiently to another device, such as, for example, the server 104. The mobile device 108 (or any other client device 106-114) can function as a spirometer to measure an exhalation and then determine the body composition of a person. The mobile device 108 (or any other client device 106-114) can trigger the information transmission between itself and server 104. The mobile device 108 (or any other client device 106-114) can provide a real-time, user-friendly, and noninvasive body composition analysis.

Although FIG. 1 illustrates one example of a system 100, various changes can be made to FIG. 1. For example, the system 100 could include any number of each component in any suitable arrangement. In general, computing and communication systems come in a wide variety of configurations, and FIG. 1 does not limit the scope of this disclosure to any particular configuration. While FIG. 1 illustrates one operational environment in which various features disclosed in this patent document can be used, these features could be used in any other suitable system.

The processes and systems provided in this disclosure allow for a client device or a server to estimate body composition. In certain embodiments, a client device (client device 106-114) can determine the body composition of a person. In other embodiments, a client device (client device 106-114) receives the forced breath of a user and forwards the data to the server 104 that determine the body composition of a person.

Figure 2:
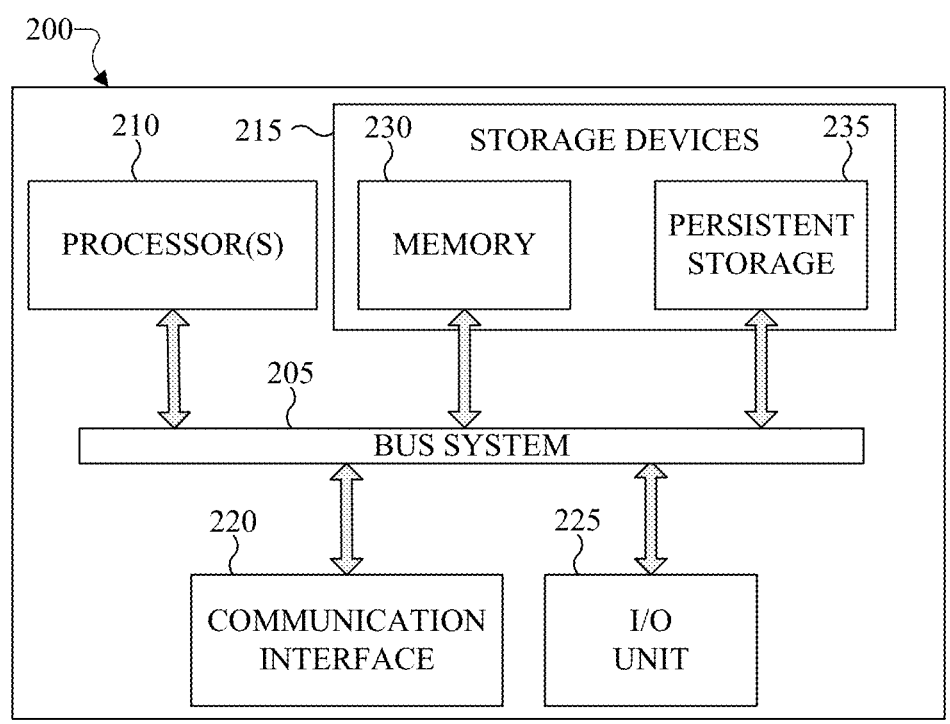
FIG. 2 illustrates an example electronic device server in accordance with an embodiment of this disclosure.
Figure 3:
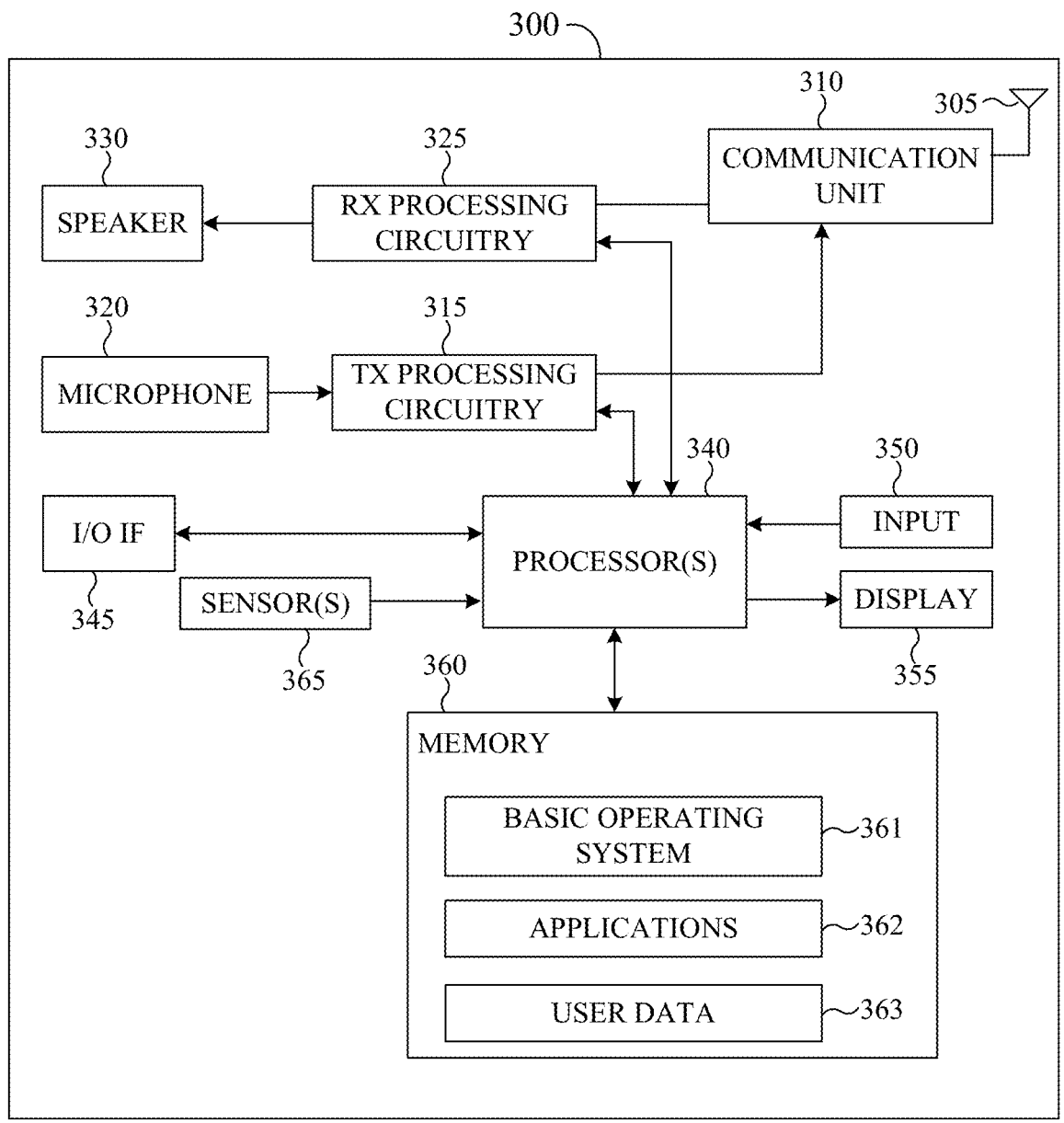
FIG. 3 illustrates an example electronic device in accordance with an embodiment of this disclosure.

FIGS. 2 and 3 illustrate example devices in a computing system in accordance with an embodiment of this disclosure. In particular, FIG. 2 illustrates an example server 200, and FIG. 3 illustrates an example electronic device 300. The server 200 could represent the server 104 in FIG. 1, and the electronic device 300 could represent one or more of the client devices 106-114 in FIG. 1.

Server 200 can represent one or more local servers, one or more body composition estimation server, or one or more call in body composition estimation server. As shown in FIG. 2, the server 200 includes a bus system 205 that supports communication between at least one processor(s) 210, at least one storage device(s) 215, at least one communications interface 220, and at least one input/output (I/O) unit 225.

The processor 210 executes instructions that can be stored in a memory 230. The processor 210 can include any suitable number(s) and type(s) of processors or other devices in any suitable arrangement. Example types of processor(s) 210 include microprocessors, microcontrollers, digital signal processors, field programmable gate arrays, application specific integrated circuits, and discreet circuitry.

The memory 230 and a persistent storage 235 are examples of storage devices 215 that represent any structure(s) capable of storing and facilitating retrieval of information (such as data, program code, or other suitable information on a temporary or permanent basis). The memory 230 can represent a random access memory or any other suitable volatile or non-volatile storage device(s). The persistent storage 235 can contain one or more components or devices supporting longer-term storage of data, such as a ready only memory, hard drive, Flash memory, or optical disc.

The communications interface 220 supports communications with other systems or devices. For example, the communications interface 220 could include a network interface card or a wireless transceiver facilitating communications over the network 102. The communications interface 220 can support communications through any suitable physical or wireless communication link(s).

The I/O unit 225 allows for input and output of data. For example, the I/O unit 225 can provide a connection for user input through a keyboard, mouse, keypad, touchscreen, or other suitable input device. The I/O unit 225 can also send output to a display, printer, or other suitable output device.

Note that while FIG. 2 is described as representing the server 104 of FIG. 1, the same or similar structure could be used in one or more of the various client devices 106-114. For example, a desktop computer 106 or a laptop computer 112 could have the same or similar structure as that shown in FIG. 2.

FIG. 3 illustrates an electronic device 300 in accordance with an embodiment of this disclosure. The embodiment of the electronic device 300 shown in FIG. 3 is for illustration only and other embodiments could be used without departing from the scope of this disclosure. The electronic device 300 can come in a wide variety of configurations, and FIG. 3 does not limit the scope of this disclosure to any particular implementation of an electronic device. In certain embodiments, one or more of the devices 104-114 of FIG. 1 can include the same or similar configuration as electronic device 300.

In certain embodiments, electronic device 300 is useable with data transfer applications, such as estimating body composition. The electronic device 300 can be a mobile communication device, such as, for example, a wireless terminal, a desktop computer (similar to desktop computer 106 of FIG. 1), a mobile device (similar to mobile device 108 of FIG. 1), a PDA (similar to PDA 110 of FIG. 1), a laptop (similar to laptop computer 112 of FIG. 1), a tablet (similar to tablet computer 114), and the like.

As shown in FIG. 3, the electronic device 300 includes an antenna 305, a communication unit 310, a transmit (TX) processing circuitry 315, a microphone 320, and a receive (RX) processing circuitry 325. The communication unit 310 can include, for example, a RF transceiver, a BLUETOOTH transceiver, a WI-FI transceiver, ZIGBEE, infrared, and the like. The electronic device 300 also includes a speaker 330, a processor 340, an input/output (I/O) interface 345, an input 350, a display 355, a memory 360, a sensor(s) 365, and a biometric scanner 370. The memory 360 includes an operating system (OS) 361, applications 362, and user data 363.

The communication unit 310 receives, from the antenna 305, an incoming RF signal transmitted such as a BLUETOOTH or WI-FI signal from an access point (such as a base station, Wi-Fi router, Bluetooth device) of the network 102 (such as a Wi-Fi, Bluetooth, cellular, 5G, LTE, LTE-A, WiMAX, or any other type of wireless network). The communication unit 310 can down-convert the incoming RF signal to generate an intermediate frequency or baseband signal. The intermediate frequency or baseband signal is sent to the RX processing circuitry 325 that generates a processed baseband signal by filtering, decoding, or digitizing the baseband or intermediate frequency signal, or a combination thereof. The RX processing circuitry 325 transmits the processed baseband signal to the speaker 330 (such as for voice data) or to the processor 340 for further processing (such as for web browsing data and remittance).

The TX processing circuitry 315 receives analog or digital voice data from the microphone 320 or other outgoing baseband data from the processor 340. The outgoing baseband data can include web data, e-mail, or interactive video game data. The TX processing circuitry 315 encodes, multiplexes, digitizes, or a combination thereof, the outgoing baseband data to generate a processed baseband or intermediate frequency signal. The communication unit 310 receives the outgoing processed baseband or intermediate frequency signal from the TX processing circuitry 315 and up-converts the baseband or intermediate frequency signal to an RF signal that is transmitted via the antenna 305.

The processor 340 can include one or more processors or other processing devices and execute the OS 361 stored in the memory 360 in order to control the overall operation of the electronic device 300. For example, the processor 340 could control the reception of forward channel signals and the transmission of reverse channel signals by the communication unit 310, the RX processing circuitry 325, and the TX processing circuitry 315 in accordance with well-known principles. The processor 340 is also capable of executing other applications 362 resident in the memory 360, such as, one or more applications for remittance, fraud detection, and the like.

The processor 340 can execute instructions that are stored in a memory 360. The processor 340 can include any suitable number(s) and type(s) of processors or other devices in any suitable arrangement. For example, in some embodiments, the processor 340 includes at least one microprocessor or microcontroller. Example types of processor 340 include microprocessors, microcontrollers, digital signal processors, field programmable gate arrays, application specific integrated circuits, and discreet circuitry The processor 340 is also capable of executing other processes and programs resident in the memory 360, such as operations that receive, store, and timely instruct by providing image capturing and processing. The processor 340 can move data into or out of the memory 360 as required by an executing process. In some embodiments, the processor 340 is configured to execute plurality of applications 362 based on the OS 361 or in response to signals received from eNBs or an operator. The processor 340 is also coupled to the I/O interface 345 that provides the electronic device 300 with the ability to connect to other devices, such as client devices 106-114. The I/O interface 345 is the communication path between these accessories and the processor 340.

The processor 340 is also coupled to the input 350 and the display 355. The operator of the electronic device 300 can use the input 350 to enter data or inputs into the electronic device 300. Input 350 can be a keyboard, touch screen, mouse, track ball, voice input, or other device capable of acting as a user interface to allow a user in interact with electronic device 300. For example, the input 350 can include voice recognition processing thereby allowing a user to input a voice command via microphone 320. For another example, the input 350 can include a touch panel, a (digital) pen sensor, a key, or an ultrasonic input device. The touch panel can recognize, for example, a touch input in at least one scheme among a capacitive scheme, a pressure sensitive scheme, an infrared scheme, or an ultrasonic scheme. Input 350 can be associated with sensor(s) 365 and/or a camera by providing additional input to processor 340. In certain embodiments, sensor 365 includes inertial sensors (such as, accelerometers, gyroscope, and magnetometer), optical sensors, motion sensors, cameras, pressure sensors, heart rate sensors, altimeter, breath sensors (such as microphone 320), and the like. The input 350 can also include a control circuit. In the capacitive scheme, the input 350 can recognize touch or proximity. The display 355 can be a liquid crystal display (LCD), light-emitting diode (LED) display, optical LED (OLED), active matrix OLED (AMOLED), or other display capable of rendering text and/or graphics, such as from websites, videos, games, images, and the like.

The memory 360 is coupled to the processor 340. Part of the memory 360 could include a random access memory (RAM), and another part of the memory 360 could include a Flash memory or other read-only memory (ROM).

The memory 360 can include persistent storage (not shown) that represents any structure(s) capable of storing and facilitating retrieval of information (such as data, program code, and/or other suitable information on a temporary or permanent basis). The memory 360 can contain one or more components or devices supporting longer-term storage of data, such as a ready only memory, hard drive, Flash memory, or optical disc. The memory 360 also can contain user data 363 that includes profile data and user history data. User data 363 can also contain data received from sensor 365. User data 363 can biographical and biometric data.

Electronic device 300 further includes one or more sensor(s) 365 that can meter a physical quantity or detect an activation state of the electronic device 300 and convert metered or detected information into an electrical signal. In certain embodiments, sensor 365 includes inertial sensors (such as accelerometers, gyroscopes, and magnetometers), optical sensors, motion sensors, cameras, pressure sensors, heart rate sensors, altimeter, breath sensors (such as microphone 320), and the like. For example, sensor 365 can include one or more buttons for touch input, (such as on a headset or the electronic device 300), a camera, a gesture sensor, a gyroscope or gyro sensor, an air pressure sensor, a magnetic sensor or magnetometer, an acceleration sensor or accelerometer, a grip sensor, a proximity sensor, a color sensor, a bio-physical sensor, a temperature/humidity sensor, an illumination sensor, an Ultraviolet (UV) sensor, an Electromyography (EMG) sensor, an Electroencephalogram (EEG) sensor, an Electrocardiogram (ECG) sensor, an Infrared (IR) sensor, an ultrasound sensor, an iris sensor, a fingerprint sensor, and the like. The sensor 365 can further include a control circuit for controlling at least one of the sensors included therein. The sensor(s) 365 can be used to determine an orientation and facing direction, as well as geographic location of the electronic device 300. Any of these sensor(s) 365 can be located within the electronic device 300 or another electronic device in communication with the electronic device 300.

In certain embodiments, sensor 365 includes a SpO2 sensor. The SpO2 sensor estimates the arterial oxygen saturation based on pulse oximetry. For example, the SpO2 sensor estimates the blood-oxygen saturation by approximating the percentage of hemoglobin molecules in the arterial blood that are saturated with oxygen. The SpO2 sensor can include light emitting diodes that shine both red and infrared light through the tissue of an extremity such as a finger, toe, or ear, of a person. The blood, tissue, and bone at the application site absorb much of the light. A portion of the light passes through the blood, tissue, and bone of the extremity. The light that passes through the extremity is received by a light-sensitive detector opposite the light source. The light-sensitive detector measures the amount of red and infrared light, and calculates the amount absorbed. The arterial blood is the one of the only light absorbing component that changes over short periods of time. The amount of arterial blood changes over short periods of time is due to pulsations of the heart pumping the blood through the body. The SpO2 sensor can isolate the arterial blood from the other components of the extremity, by calculating the slight changes in the amount of red and infrared light absorbed by the extremity. Based on the changes in the red and infrared light absorbed by the extremity the SpO2 sensor can estimate oxygenation level of the arterial blood.

In certain embodiments, sensor 365 includes a radar sensor. A radar sensor is able to determine information about the target by emitting electromagnetic signals towards a target, and then detecting the reflected electromagnetic signals from the target. For example, the radar sensor can detect respiration rates of a person or respiration patterns a person or both. The radar sensor detects when a person breaths. The radar sensor can even detect various factors associated with each detected breath. For example, the radar sensor can detect a forced breath as well as the magnitude of the breath such as an approximate amount of air exhaled over a particular time period.

Although FIGS. 2 and 3 illustrate examples of devices in a computing system, various changes can be made to FIGS. 2 and 3. For example, various components in FIGS. 2 and 3 could be combined, further subdivided, or omitted and additional components could be added according to particular needs. As a particular example, the processor 340 could be divided into multiple processors, such as one or more central processing units (CPUs) and one or more graphics processing units (GPUs). In addition, as with computing and communication networks, electronic devices and servers can come in a wide variety of configurations, and FIGS. 2 and 3 do not limit this disclosure to any particular electronic device or server.

Figure 4:
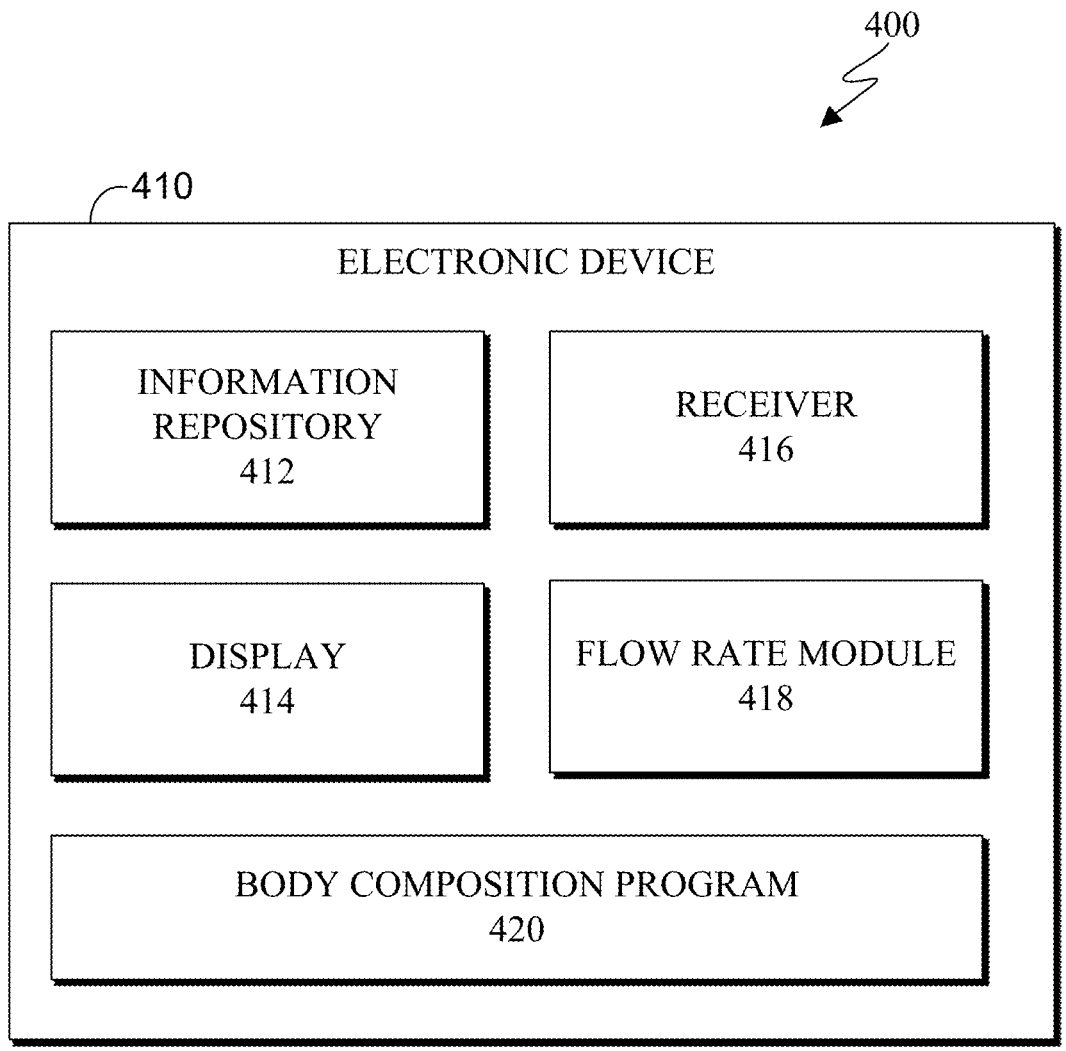
FIG. 4 illustrates an example block diagram of a forced breathing body composition analyzing device in accordance with an embodiment of this disclosure.

FIG. 4 illustrates an example block diagram of a forced breathing body composition analyzing device in accordance with an embodiment of this disclosure. The embodiment of the system architecture 400 shown in FIG. 4 is for illustration only. Other embodiments could be used without departing from the scope of the present disclosure.

System architecture 400 illustrates a high-level overview of an embodiment of the present disclosure to detect and capture a forced breath of a user and determine the body composition therefrom. System architecture 400 illustrates electronic device 410. Electronic device 410 can be configured similar to any of the one or more client devices 106-114 of FIG. 1, and can include internal components similar to that of electronic device 300 of FIG. 3. In certain embodiments, electronic device 410 can detect and capture a forced breath of a user and determine the body composition of the person. In certain embodiments, electronic device 410 can detect and capture a forced breath of a user, transmits the data to a server (similar to server 104 of FIG. 1) to determine the body composition of the person.

In certain embodiments, electronic device 410 is a mobile phone similar to mobile device 108, of FIG. 1. For example, electronic device 410 is capable of making and receiving phone calls, sending and receiving SMS text messaging, and capable of browsing the Internet. For instance, electronic device 410 can be a smart phone with access to third party applications. For another instance, electronic device 410 can be a feature phone, with applications that are propriety to the manufacturer of the electronic device. In certain embodiments, electronic device 410 is a computer device similar to the desktop computer 106, the laptop computer 112, and the tablet computer 114, of FIG. 1. In certain embodiments, electronic device 410 is a head mounted display, and worn by the user. In certain embodiments, electronic device 410 is a watch, a wristband, or a fitness tracker. Electronic device 410 includes an information repository 412, a display 414, a receiver 416, flow rate module 418, and a body composition program 420. Electronic device 410 can also include speakers, provide haptic feedback, and support other feedback techniques.

Information repository 412 can be implemented using any architecture known in the art such as, for example, a relational database, an object-oriented database, or one or more tables, or a combination thereof. Information repository 326 stores data to assist body composition program 420 in determining the body composition of a user by including look-up tables, databases, charts, graphs, functions, equations, and the like that the body composition program 420 can access. Information repository 412 includes user profile data such as demographic data or demographic factors, gender, age, height, medical conditions, health factors, previous body composition analysis, clinically calculated parameters (if available), and the like. Medical conditions can include known ailments and disorders, diagnosed by a medical professional that can affect the received data of the user to determine the body composition of the user. For instance, the user only has a single lung or suffers from Asthma, COPD, or other lung related disorders. Health factors can be received from various sensors within the electronic device or received from a second device. Health factors can include derived data, information inputted by the user or received data related to the user, or a combination there of. Health factors can include physical activities, sleep patterns, food and drink intake, stress levels and the like. For example, a pedometer associated with the electronic device 410 can be used to measure the number of steps the user took during a given time period. In another example a heart monitor can be used to determine the activity level of the user. In another example, a movement detector can be used to determine the activity level of the user. Previous body composition analysis and breath analysis can be inputted into the information repository as a baseline for the body composition program 420, to more accurately determine the body composition of a user and more particularly the percentage of visceral fat a user has. While depicted in electronic device 410, information repository 412 can be on a server, or a remote server, or a "cloud" of computers interconnected by one or more networks utilizing clustered computers and components to act as a single pool of seamless resources, accessible to body composition program 420 via network 102 of FIG. 1.

Display 414 is similar to display 355 of FIG. 3. In certain embodiments, display 414 is a single display and affixed to the electronic device. In certain embodiments, display 414 is affixed to a head mounted display and can project virtual reality (VR), augmented reality (VR) and the like. In certain embodiments, display 414 is a user interface allowing the user to provide demographic data and additional information to improve the body composition analysis, as well as provide guidance and the results of the body composition analysis. For example, display 414 can depict a real-time visualization of data received from receiver 416. For example, if receiver 416 is similar to a spirometer, display 414 can illustrate a graphical representation (similar to the graph of FIG. 5A depicted below) and in real-time illustrate the users forced breath in comparison to an idealized breath. By illustrating users real-time breath alongside an idealized breath, display 414 can provide user feedback and guidance to improve the data acquisition of the receiver 416. Display 414 can also depict the results of the body composition analysis by the body composition program 420.

Receiver 416 is similar to the microphone 320 of FIG. 3, or the sensor 365 of FIG. 3, or both. Receiver 416 is capable of detecting and capturing various parameters of a forceful breath. Receiver 416 can receive and capture breath data, similar to how a spirometry test receives breath data. During a spirometry test, a user forcefully exhales through a flow measuring device, such as a spirometer. A spirometer measures the instantaneous flow and the cumulative exhaled volume. Receiver 416 is capable of detecting and capturing various parameters of a forceful breath of a user. A forceful exhale occurs when (i) the user inhales enough air to fill the lungs as much as possible, and then (ii) the user forcefully exhales the entire volume of air out of the lungs. If the receiver 416 is positioned a distance from the mouth of a user while the user can forcefully exhale, the receiver 416 can detect the exhale. For instance, after taking a forced inhalation the receiver 416 captures the quick and forceful exhalation as the entire capacity of air within the lungs of the user is depleted. In certain embodiments, the distance the receiver 416 is from the mouth of the user is predetermined. In other embodiments the distance the receiver 416 is from the mouth of the user is changeable between each forced breath received. In certain embodiments, the distance the receiver 416 is from the mouth of the user is fixed during the forced breath and data acquisition. In certain embodiments, the location of the receiver 416 in relation to the mouth of the user is predetermined.

In certain embodiments the display 414 can guide a user as to the appropriate distance to place the receiver 416 in relation to the mouth of the user. For example, display 414 can guide the user to adjust the distance of the receiver 416 with respect to the mouth of the user. The body composition program 420, using internal sensors of the electronic device 410, measures the geometric distance between the receiver 416 and the mouth of the user by identifying the position and orientation of the electronic device 410, with respect to body coordinate system centered at the shoulder of the user. For instance, when the electronic device 410 is held in front of the mouth of the user, sensors such as accelerometer, gyroscope, magnetometer (similar to sensors 365 of FIG. 3) provide position and orientation information of the electronic device 410 with respect to the shoulder of the user. Relative distance between the mouth and the receiver 416 can be approximated by including the position and orientation of the electronic device 410 with the length of the upper-arm and forearm, and distance between the shoulder and the mouth of the user. The length of the upper-arm and forearm, and distance between the shoulder and the mouth of the user can be predetermined based on approximate values based on the biographical and demographical data of the user or inputted by the user.

In another example, the body composition program 420 utilizes individual templates of the forced breathing pattern when the electronic device 410 is positioned as close as possible from the mouth, such as touching the chin, check, or lips of the user. The template of the forced breathing pattern is used as a baseline. Once the body composition program 420 learns this forced breathing pattern, it can estimate the distance between receiver 416 and the user by computing similarity between the template pattern and the current breathing pattern based on time-series pattern matching algorithms such as dynamic time warping or the like.

In certain embodiments, the receiver 416 is a microphone that receives sound waves such as breathing or voice data and converts the sound waves into electrical signal. Specifically, the acoustic waves traveling through the air interact with a transducer inside the microphone in some measurable way. With a piezoelectric mic for example, sound waves apply pressure to a polarized crystal causing it to generate a voltage. This change in voltage is what is measured at the surface of the crystal. The more pressure applied to the crystal, the greater the voltage generated. Receiver 416 can be a microphone similar to a dynamic microphone, a condenser microphone, a piezoelectric microphone, or the like. The microphone can record and save the exhalation in the information repository 412, and transmit the audio data to the flow rate module 418 or to a communication unit, similar to the communication unit 310 of FIG. 3, and/or transmit the audio data to a server (similar to server 200 of FIG. 2), for processing.

In certain embodiments, receiver 416 is a radar sensor that emits and detects radar signals. A radar sensor can detect information about a targeted user by emitting electromagnetic signals towards the user, and then detecting the reflected electromagnetic signals from the user. For example, the radar sensor can detect respiration rates and parameters associated therewith of a person. The radar sensor can capture and save the exhalation in the information repository 412, and transmit the data to the flow rate module 418 or to a communication unit, similar to the communication unit 310 of FIG. 3, and/or transmit the audio data to a server (similar to server 200 of FIG. 2), for processing.

In certain embodiments, receiver 416 is an infrared detector. The infrared detector generates a heat map that can map various parameters of a forced exhale of a user. Since the exhale is a different temperature than the ambient temperature the infrared detector can map the magnitude and volume of the exhale over a time period. The infrared detector captures and saves the exhalation in the information repository 412, and transmits the data to the flow rate module 418 or to a communication unit, similar to the communication unit 310 of FIG. 3, to transmit the audio data to a server (similar to server 200 of FIG. 2) for processing.

In certain embodiments, receiver 416 can include a SpO2 sensor that can detect the pulse and oxygenation of the blood of the user. The SpO2 sensor estimates the arterial oxygen saturation based on pulse oximetry. The SpO2 sensor can also determine the pulse of a user. In certain embodiments, the SpO2 sensor is a photoplethysmogram (PPG) sensor. The pulse and oxygenation of the blood can be utilized to identify various breathing conditions or disorders a user might suffer from. Based on identifying a particular breathing disorder, one or more parameters associated with the received forced breath can be altered based on the data received from the SpO2 sensor. By altering one or more parameters associated with the received forced breath, the body composition analysis is altered. That is, the SpO2 sensor can provide additional information to the body composition program 420 to refine the body composition analysis. The pulse and oxygenation of the blood readings captured by the SpO2 sensor can be saved within the information repository 412. The pulse and oxygenation of the blood readings captured by the SpO2 sensor can be utilized by the body composition program 420 to refine various parameters associated with the forced breath data to accurately determine the body composition.

In certain embodiments, receiver includes a bioelectrical impedance analyzer (BIA). A BIA performs body impedance analysis by determining the electrical impedance of an electric current through body tissues that can then be used by the body composition program 420 to estimate total body water within a user. In certain embodiments, electronic device 410 can be in communication with a wristband that emits electrical currents through electrodes into the user. If the body impedance measurement is performed within a wristband, the electronic device 410 can receive measurements of the upper body of the user. Breathing parameters acquired by the receiver 416 are complemented by the BIA measurements thereby allowing the body composition program 420 to further refine the body composition analysis of the user.

Flow rate module 418 determines the flow rate associated with the forced breath of the user. In certain embodiments, the flow rate module 418 and the body composition program 420 are a singular component of electronic device 410. Flow rate module 418 receives the forced breath data from the receiver 416. If the receiver 416 includes a microphone, the flow rate module 418 calculates the exhaled flow rate by estimating the noise of the exhale of the user and the ambient noise around the user. For example, the flow rate module 418 can determine pressure change as the air exits the mouth of the user during a forced exhale. The change in pressure can be related to flow.

Background noise, such as ambient noise, and the distance between the electronic device 410 and the mouth of the user can affect the accuracy of the parameter estimation. In certain embodiments, when the user starts to measure body composition, via a forced exhale, the body composition program 420 instructs the user to keep the electronic device 420 as close to the mouth of the user as possible. As discussed above, body composition program 420 detects and derives the distance between the electronic device 410 and the mouth of the user. If the distance is more than a threshold, the body composition program 420 can indicate to the user, that the receiver 416 is to be placed closer to the mouth of the user. The body composition program 420 can indicate the location of the receiver 416 with respect to the mouth of the user via display 414, an audible notification or the like. In certain embodiments, the distance between the mouth of the user and the receiver 416 are touching or nearly touching. Once the device is kept closer to the mouth of the user, the user performs a forced breath. The forced breath generates an exhale sound that powers the majority of all background and ambient noises, such as an air conditioner.

In certain embodiments, air pressure loss due to non-zero distance (D) between the mouth of the user and the electronic device 410 device, specifically that of the receiver 416, is compensated by using inverse radiation modeling. Inverse radiation modeling can also compensate reflections caused in and around user's head. The transfer function from the receiver 416 to mouth of the user can be approximated by using equation (1).

$$H(j\omega) \sim \frac{j\omega C_{head}}{D} e^{-\frac{j\omega D}{c}}. \qquad \text{Equation (1)}$$

In equation 1, c is the speed of sound, $C_{head}$ is the head circumference of the user. In certain embodiments, $C_{head}$ is received as an input by the user. In certain embodiments, $C_{head}$ is automatically approximated based on the height, weight, and demographic information of the user. Applying inverse of the above transfer function provides a time domain signal that can be filtered, using a low pass filter, to approximate the air pressure from mouth to the device microphone.

Noise parameters can be factored in several ways. In certain embodiments, the captured audio is segmented into 30 ms frames (f). For example, if a forced exhale lasts up to 8 seconds, the flow rate module 418 segments the forced exhale into m=266 frames, where the 266 frames is a single measurement window (w). If one embodiment uses 16 KHz sampling rate, then each frame (f) will have n=800 samples (s). The flow rate module 418 compute root mean square (RMS) value for each frame as $ms(f) = \sqrt{\sum_{i=1}^{n} s_i^2 / n}$. The flow rate module 418 then computes the RMS ratio to identify noise window from the exhale window, by using equation (2).

$$RMSratio(w) = \frac{1}{m} * \sum_{i=1}^{m} I_{[rms(f_i) > 0.5 * \overline{rms(w)}]}. \qquad \text{Equation (2)}$$

In equation (2)

$I_{[a>b]} = \begin{cases} 1, & \text{if } a > b \\ 0, & \text{otherwise} \end{cases}$ is the indicator function, and the notion $\overline{rms(w)}$ is the average RMS value of the window w.

Equation (2) yields background noise between zero and one. Instances of continuous background noise, such as appliances, the result of equation (2) is close to 1. Instances of short-term discrete noises, such as a door knocking, the result of equation (2) is close to zero. The exhalation sound of a forced breath is between the two extremes, such as 0.5. Therefore, background noise can be discarded from the analysis by using an appropriate threshold on the RMSratio (w) regardless of the distance between the device and the mouth.

In certain embodiments, flow rate module 418 computes variance ($var_i$) of acoustic signal in a frame ($f_i$) to factor out background noises. Variance reflects how far the amplitude of the audio within the frame are spread out. For example, a normalization of variance over a window (w) can be computed to handle issues of different variance from noise sources. For example, by computing a normalization of variance over a window (w) ensures the variance feature are more robust while canceling out the noise from the forced breathing signal.

Normalization is performed based on equation (3).

$$\overline{\mathrm{var}(f_1)} = \frac{\mathrm{var}_i - \mathrm{var}_{mean}}{\mathrm{var}_{mean} - \mathrm{var}_{min}}. \quad \text{Equation (3)}$$

Based on equation (3) normalized variance of the most of the noise window will be lower than a certain threshold. In certain embodiments the certain threshold is, 0.5. Audio signal from a forced exhale conducted in front of the receiver 416 has a higher variance than the background noise. Therefore, if the variance value is below a certain threshold, the window can be discarded as noise.

Sound generated by a forced exhalation is proportional to the air flow from the mouth opening of the user during the exhalation. The flow reduces with the progression of exhalation as the lung air pressure gradually becomes lower. The sound energy also will be lower with the progression of exhalation as the lung air pressure diminishes. Therefore, once the window of interest is identified, the sound signal can be converted into the breathing signal in several ways including time domain envelope computation, resonance tracking in frequency domain spectrogram, or by computing linear predictive coding (LPC) coefficients and gains. The upper envelope of the signal can be a reasonable approximation of the air pressure exhaled from the mouth opening in front of the receiver 416 as a representation of the overall signal power. In certain embodiments the resonance tracking starts with computing FFT over an overlapping frame of the audio signal, and taking the magnitude spectrogram of the signal. Then average resonance can be tracked by computing sustained maxima over a certain threshold of FFT in each frame. For example, the sustained maxima can be greater than 300 ms, while the threshold can be greater than 20% of the global maximum of FFT in each frame. A linear prediction coding algorithm can be applied over the overlapping frames with several LPC model orders, such as 2, 4, 8, or 16. The processed signal can further be refined by low pass filters for more accurate flow rate feature extraction. The flow rate module 418 can then extract flow rate features for each audio frame. Moreover, the volumetric features are calculated by integrating the flow with respect to time. Finally, extracted breathing features can further be calibrated by using regression techniques such as bagged decision tree combined with one or more other machine learning models, such as a Conditional Random Field.

If the receiver 416 includes a radar sensor, the flow rate module 418 calculates the exhaled flow rate by detecting movements of the chest of a user as the user breaths. If the receiver 416 includes an infrared detector, the flow rate module 418 calculates the exhaled flow rate by deriving the temperature gradient and variations associated with each breath of the user.

Figure 5:
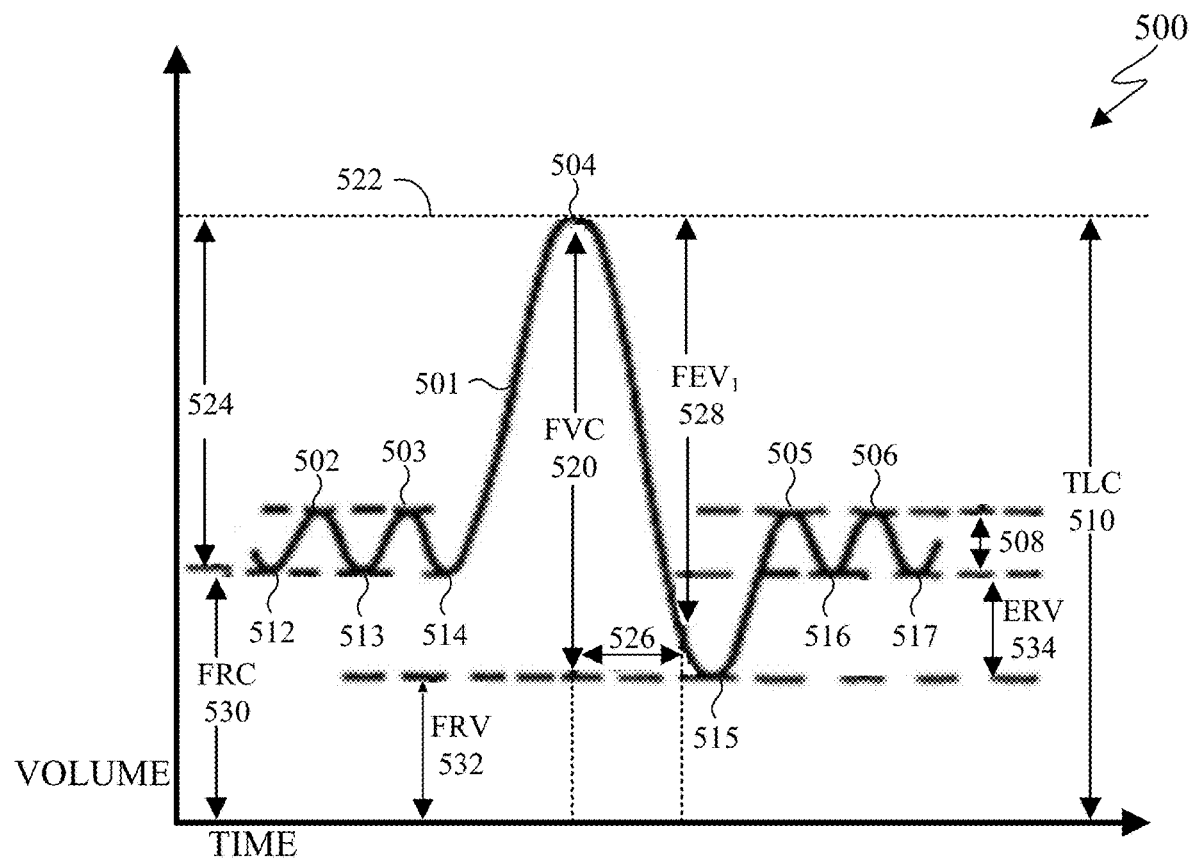
FIG. 5 illustrates a graphical representation of a breathing signal in accordance with an embodiment of this disclosure.

Respiratory functions can be monitored by the length, volume, magnitude of an inhalation, magnitude of an exhalation, and the like. Understanding the flow rate of the lungs can illustrate how much air is going into the lungs and how rapidly air is inhaled and exhaled in the lungs (airflow). In certain embodiments, flow rate module 418 derives the flow rate as the air is forcibly exhaled by the user. The flow rate module 418 derives the flow rate by calculating the received data associated with the forced exhale in relation to a time frame, analyzing the frequency of the exhale, and measuring the ambient noise. The flow rate module 418 derives the flow rate of the forced breath in relation to volume and time of the forced exhale. For example, the breathing pattern can be depicted as a sinusoidal function based on the derived volume of air of each exhale in relation to time, as depicted in FIG. 5 below. Based on the derived flow rate, flow as a function of time, the flow rate module 418 can derive additional information associated with the forced breathing. For example, flow rate module 418 can derive the volume rate of the exhale, volume as a function of time. For another example, flow rate module 418 can derive the flow as a function of volume. FIGS. 6A through 6D illustrate graphs of the flow as a function of volume, as derived by the flow rate module 418.

Body composition program 420 performs the body composition analysis by extrapolating and analyzing various forced breathing parameters of the derived flow rate. The flow rate module 418 can determine various factors such as a forced vital capacity (FVC), the expiratory reserve volume (ERV), forced expiratory volume in one second ($FEV_1$), and a peak expiratory flow (PEF), and the like. FVC is the total exhaled volume of air during a forced breath. ERV is the difference in the reserve volume of air that remains in the lungs that differs between a normal exhale and a forced breath exhale. $FEV_1$ is volume of air exhaled in one second after the peak of a forced exhalation. PEF is the maximum flow velocity reached during the forced breathing. Body composition program 420 can utilize the detected $FEV_1$, FVC, and the ratio of $FEV_1$ and FVC to quantify the degree of airflow restriction due to lung diseases and visceral fat. For example, if the user has visceral fat that is accumulated around the abdominal organs, the visceral fat creates obstructions to the forced breathing that limit the detected parameters. Body composition program 420 then identifies and calculates the level of restriction of the air flow when the user performs a forced breath. Forced breathing provides the body composition program 420 a more accurate analysis of the amount of visceral fat than normal breathing.

In certain embodiments, body composition program 420 receives additional data to refine the body composition analysis. For example, if the SpO2 sensor indicates low blood oxygenation, then the body composition program 420 may determine that the user suffers from a lung disease and can refine the parameters accordingly. In another example, the information repository 412 can include information indicating a specific ailment or lung disease that the user possesses. If the information repository 412 indicates a specific ailment or lung disease the user suffers from, then the body composition program 420 can utilize that information and refine the parameters accordingly.

In certain embodiments, body composition program 420 determines the composition of an individual by building and analyzing a regression model of predicting body fat percentage from the captured data. Body composition program 420 can personalize the regression model by incorporating personalized data from the user as well as previous body composition results. Personalized data from the user can include the age, height, and gender of the user. Additional personalized data can include the weight of the person, medical history of the person, known lung disease and the like.

In certain embodiments, body composition program 420 accesses additionally health and wellness services in order to provide a fuller health analysis for the user. For example, body composition program 420 can receive via input form the user or from a different application, medical conditions associated with the user. Health factors can also be received from various sensors within the electronic device 410 or received from a second device, such as blood pressure, a scale, physical activity monitors, sleep monitors, and the like. Based on the received health factors, body composition program 420 can display to user an overall health analysis. In certain embodiments, body composition program 420 can transmit the body composition analysis to a third application.

In certain embodiments, the body composition program 420 reports the result of the forced breath and body analysis to the user. In certain embodiments, the body composition program 420 reports the result of the forced breath and body analysis to the medical provider of the user. In certain embodiments, medical providers would be able to independently review and understand the basis of the decision of the body composition program 420, and actions taken of recommendations that are pushed to the user.

In certain embodiments, the body composition program 420 can generate potential exercise regiments or food recommendations, or both. In generating exercise regiments or food recommendations the body composition program 420 can leverage the information input by the users, collected by wearables such as a pedometer, combined with clinically set protocols (healthcare provider protocols) to ensure personalized, accurate recommendations and adjustments.

FIG. 5 illustrates a graphical representation of a breathing signal in accordance with an embodiment of this disclosure. FIG. 5 illustrates a graph 500 depicting a series of breaths a user takes over a period of time. In certain embodiments, receiver 416 is a microphone and captures audio data associated with a series of exhales including a forced breath. The flow rate module then synthesizes the data received from receiver 416 using a linear predictive analysis to extract the breath signal 501. The set of breathing parameters are identified and computed. The parameters can include (i) the total lung capacity of the user, (ii) the functional residual capacity of the lungs of the user, (iii) the $FEV_1$, (iv) the FRV, (v) the FRC, (vi) the ERV, (vii) the PEF, and the like. Thereafter a regularized regression model can estimate the body fat of the user. In a certain embodiment, the body fat percentage of a person is based on the parameters of (i) FVC, (ii) ERV, (iii) $FEV_1$, (iv) the ratio of $FEV_1$ to FVC, and (v) PEF, the age of the individual and the gender. Each parameter is adjusted based on the weight of the individual parameter. For example, the weight of the individual parameter is a factor that is used to adjust each parameter in the regression model. The weight of each parameter can be evaluated based on a gradient decent optimization or a least square function or the like. Additional parameters can be included based on known breathing disorders of the individual.

Graph 500 depicts the total lung capacity (TLC) 510. TLC 510 is the total capacity of air the lungs of an individual. Breath signal 501 depicts the volume of air inhaled and exhaled during each breath with respect to time, as captured by the receiver 416 and derived by the flow rate module 418. Breath signal 501 is a sinusoidal function that represents the volume of air within the lungs of a user in relation to time as the user breathes.

The breath signal 501 includes five breaths where each breath commences at an inhale and concludes at an exhale. The breath signal 501 is represented by a sinusoidal function where each breath is a cycle of the cycle of the sinusoidal function. The breath signal 501 rises and falls as the volume of air within the lungs increases and decreases during each breath. Crests 502, 503, 504, 505, and 506 (the highest point of the breath signal 501) are the maximum volume inhaled during each breath, while the troughs 512, 513, 514, 515, 516, and 517 (the lowest point of the breath signal 501) are the residual volume of air that remains in the lungs during an exhale. The first breath cycle commences at trough 512, through the maximum inhale at crest 502, and then the exhale commences and continues until the exhale concludes at trough 513. The second breath cycle commences at trough 513, through the maximum inhale at crest 503, and then the exhale commences and continues until the exhale concludes at trough 514. The third breath cycle commences at trough 514, through the maximum inhale at crest 504, and then the exhale commences and continues until the exhale concludes at trough 515. The fourth breath cycle commences at trough 515, through the maximum inhale at crest 505, and then the exhale commences and continues until the exhale concludes at trough 516. The fifth breath cycle commences at trough 516, through the maximum inhale at crest 506, and then the exhale commences and continues until the exhale concludes at trough 517.

The first, second, fourth, and fifth breaths, as described above, each represent a normal breath. The third breath, as described above, represents a forced breath. During periods of normal breathing, the volume of the inhaled breath at crests 502, 503, 505, and 506 are approximately the same approximate level for each breath. During such periods of normal breathing, volume 508 is the volume of air inhaled or exhaled by the user for each breath. Functional residual capacity (FRC) 530 is the residual volume of air left in the lungs after a normal inhale and exhale. For example, after a normal exhale, the FRC 530 volume of air that remains within the lungs after a normal exhale.

In contrast to normal breathing, a forced breath generates a long deep breath signal 501 that has a maximum volume at crests 504 and a minimum volume at trough 515. During a forced breath, the user inhales as much air as possible to completely fills the lungs of the user. For example, when a user takes a forced inhalation, the user can inhale more air into their lungs and expand their lungs to a maximum volume. The lungs of the user are filled to a maximum volume as indicated by TLC 510. Volume 524 is the volume of air the lungs can fill above the FRC 530. Volume 524, crest 504, and TLC 510 are the same as indicated by line 522. After the inhale from trough 514 to crest 504, the user quickly and forcefully exhales as much air as possible, trying to vacate air from the lungs. During a forced breath, FVC 520 is the total volume of air exhaled by the user in a quick burst. FVC 520 represents the volume of air in the lungs that can be exhaled following a deep inhalation. Time 526 is a one second interval of time that is measured from the crest 504 of the forced breath. For example, time 526 is measured from the moment the user stops inhaling and commences exhaling. Forced expiratory volume in one second ($FEV_1$) 528 indicates the volume of air exhaled after one second.

As indicated in graph 500 the he inhale reaches a maximum volume at line 522, and a minimum volume at forced residual volume (FRV) 532. The FRV 532 is the residual volume of air within the lungs, upon completion of the forced breath. The forced breath yields less air in the lungs as compared to the amount of residual air left in the lungs during a normal breath. For example, as FRV 532 is less than FRC 530. Expiration residual volume (ERV) 534 is the difference in the volume of air between a forced exhale and a normal exhale.

The residual air that remains in the lungs is significantly lower during a forced breath than the residual air that remains in the lungs during a normal breath. Body composition program 420 can analyze the FVC 520, $FEV_1$ 528, FRC 530, and FRV 532, to determine body composition. For example, restrictions in the breathing can be due to excess visceral fat. In certain embodiments, a restriction reduces the difference between FRC 530 and FRV 532 that essentially reduces the ERV 534. The smaller the ERV 534, can indicate whether the person suffers from excess visceral fat, based on a variety of factors such as age, height, and gender, known breathing disorders. Fat accumulated around the abdominal area of a person, can create an obstruction to the forced breathing effort and the parameters of the forced breathing can capture the severity of the deviation.

FVC 520 and $FEV_1$ 528 are two measurements indicate the functioning of the lungs of a user. For example, information repository 412 can include a listing of acceptable values for a given person based on their age, gender, and height. If the values derived for the FVC 520 and $FEV_1$ 528, by the flow rate module 418, are not within predetermined ranges then the body composition program 420 can determine that the user suffers from a lung or breathing disorder. When the body composition program 420 determines that the user suffers from a lung disease, the body composition program 420 can adjust one or more parameters in order to determine the body composition of the user. In another example, the ratio of $FEV_1$ 528/FVC 520 provides an additional indication as the functioning of the lungs. Specifically, $FEV_1$ 528/FVC 520 is the percent of the lung volume that can be exhaled in one second. If the ratio is equal to or greater than a predetermined value then the lungs are considered to be functioning in the normal range. The predetermined value is based on age, gender, and height of the individual. Therefore, if body composition program 420 determining that the ratio of $FEV_1$ 528/FVC 520 is below a predetermined value, then the body composition program 420 can identify that the user suffers from a restriction while performing a forced breath. The restriction can indicate that user has excess visceral fat as well as a breathing disorder. Body composition program 420 can also determine an approximate the severity of the restriction based on the ratio of $FEV_1$ 528 to FVC 520. In certain embodiments, the body composition program 420 can determines that the FVC 520 is an abnormal value, based on a universal predetermined value, when minimal information about the user is known. In certain embodiments, the body composition program 420 can determines that the FVC 520 is an abnormal value, analyzing the value in comparison to personalized data associated with the user. For example, if the FVC 520 is an abnormal value indicates a restriction associated with the lung functioning. Restrictions in the breathing are often be caused by excess visceral fat, if the user has no indication of a lung disease. Restrictive lung diseases can include asthma, emphysema, and COPD.

In certain embodiments, body composition program 420 can utilize the data as indicated in graph 500 to estimate the body composition of a user. For example, the body composition program 420 can analyze the FVC 520, the ERV 534, the $FEV_1$ 528, the ratio of $FEV_1$ 528 to the FVC 520, PEF, the age of the user, the gender of the user. Each variable can be multiplied by a weight parameter based on known medical history, family history, previous body composition analysis, as well as additionally received information such as the users SpO2 reading, BIA, and the like. In certain embodiments, the body composition program 420 can then use a gradient descent optimization to determine the weight parameter associated with the above discussed variables to quantify the visceral fat within the user. In certain embodiments, the body composition program 420 can use a square function to determine the quantity of visceral fat within the user. In certain embodiments, the body composition of a user to derive the body fat percentage of a user, can be expressed by the function $w_0+w_1*FVC+w_2*ERV+w_3*FEV1+w_4*(FEV_1/FVC)+w_s*PEF+w_6*age+w_7*gender+\ldots+\varepsilon$. In the function, $w_n$ represents a weight parameter associated with the user, in a regression model. Similarly, the variable $\varepsilon$ is the error factor associated with the function, to compensate for one or more factors such as a breathing disorder, and the like. In certain embodiments, body composition program 420 can utilize data collected in a clinical facility under a trained practitioner to determine each variable for a more accurate, personalized body composition of an individual. For example, a clinical spirometer device can be used to calibrate forced breathing parameters for a particular individual. In certain embodiments, body composition program 420 can track changes in body composition over time and alert user with increasing or decreasing trends of body composition of the user. In certain embodiments, the trends can be communicated to help a care-provider create or adjust an exercise regimen for improving the fitness of the user.

Figure 6A:
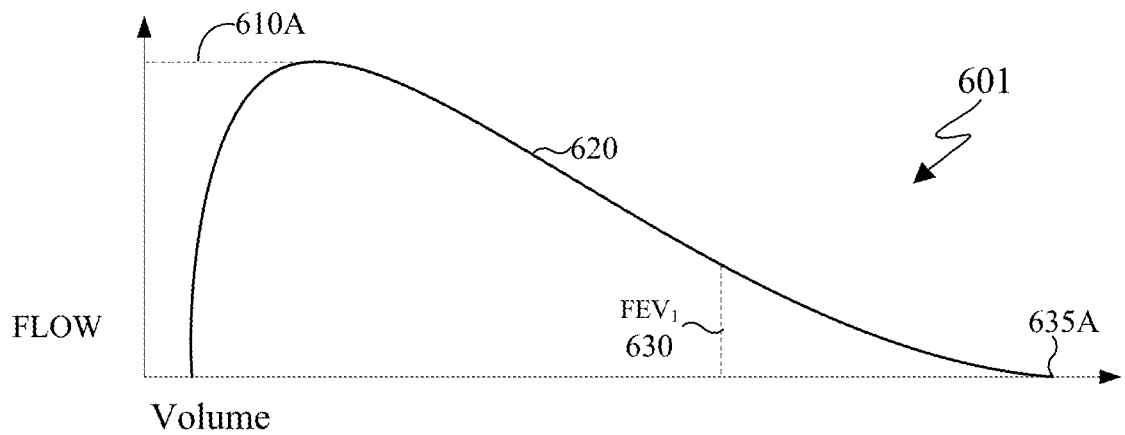
FIGS. 6A, 6B, 6C and 6D are graphs illustrating flow and volume curves with respect to lunch functions in accordance with an embodiment of this disclosure.
Figure 6B:
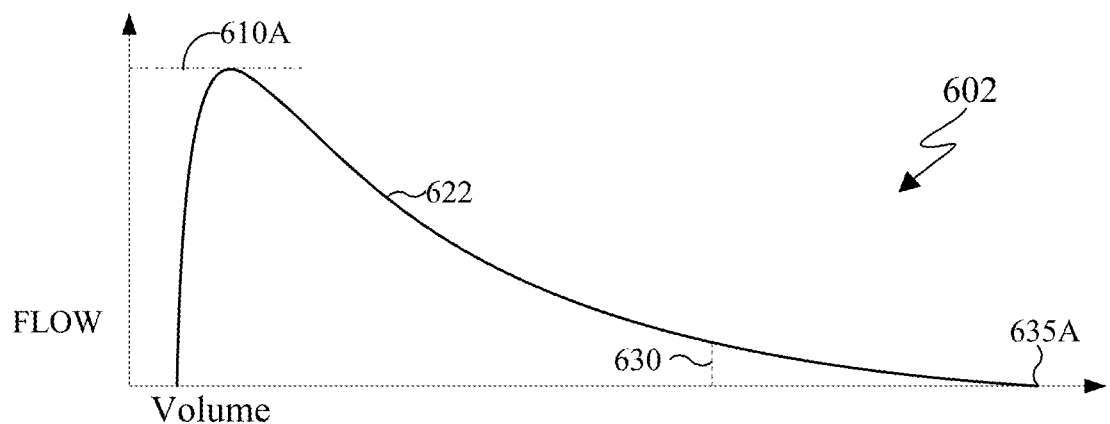
Figure 6C:
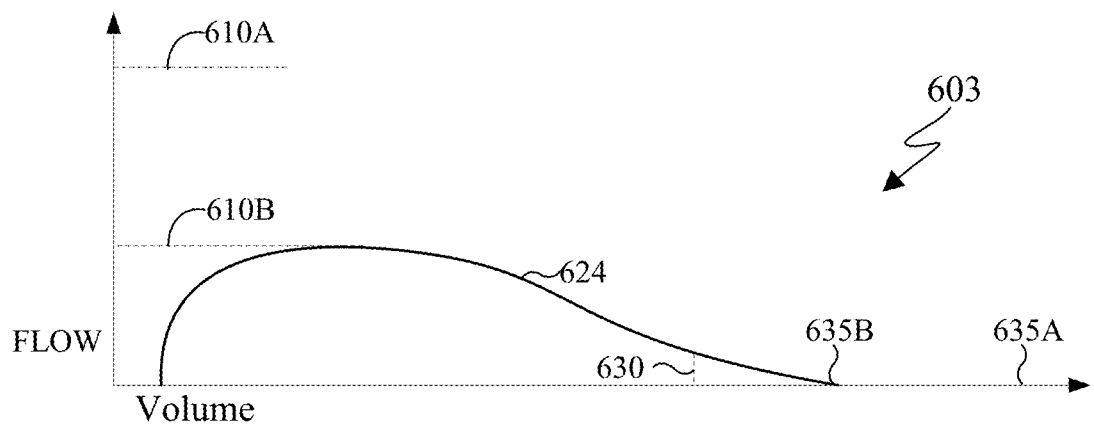
Figure 6D:
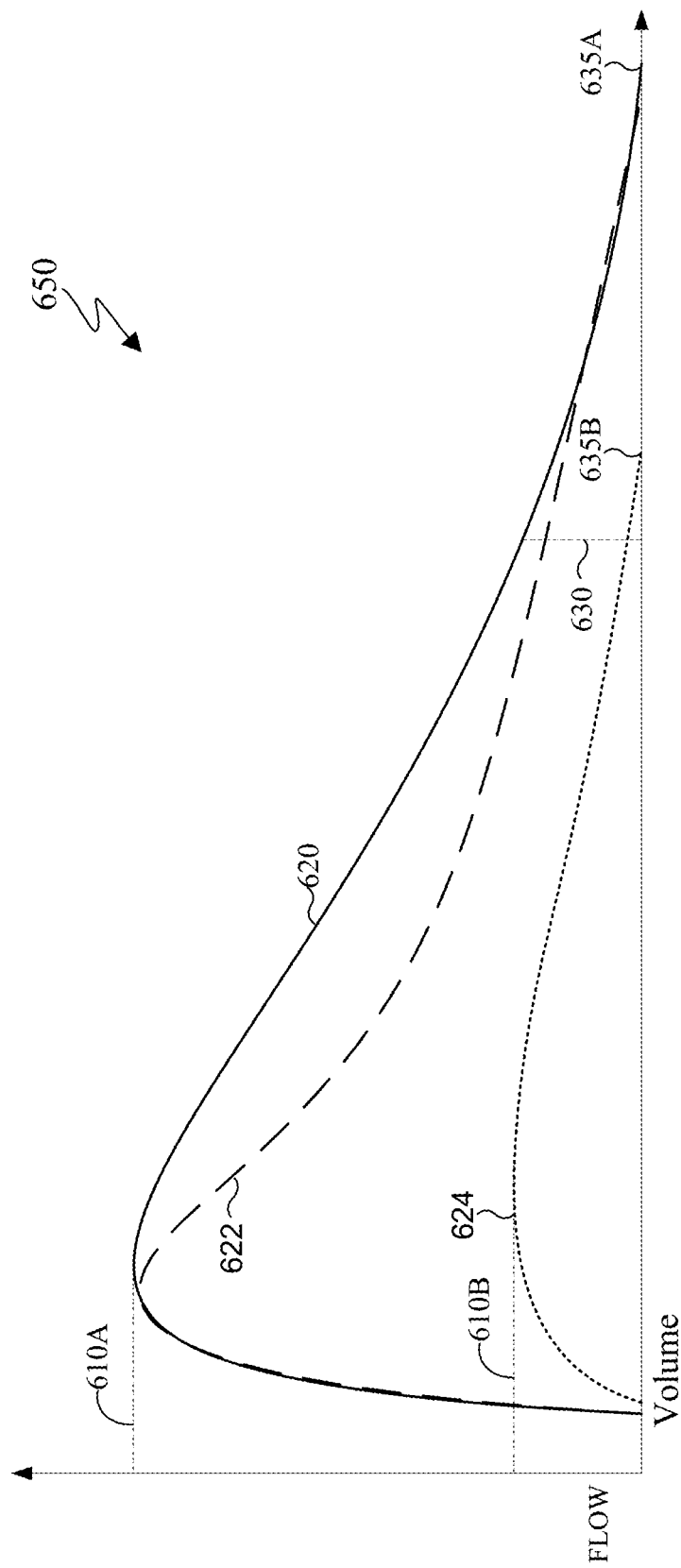

FIGS. 6A through 6D are graphs illustrating flow and volume curves with respect to lunch functions in accordance with an embodiment of this disclosure. FIG. 6A illustrates a graph of a normal forced breath curve captured using a microphone. FIG. 6B illustrates a graph of an obstructed forced breath curve. FIG. 6C illustrates a graph of a restrictive forced breath curve. FIG. 6D illustrates a graph of the normal forced breath curve of FIG. 6A, the graph of an obstructed forced breath curve of FIG. 6B, and the graph of a restrictive forced breath curve of FIG. 6C on a singular graph.

FIG. 6A illustrates a graph 601 depicting a single forced breath a user took. Receiver 416 captures the breathing data. In certain embodiments, the flow rate module synthesizes the data from receiver 416 using a linear predictive analysis to extract the forced breath 620. Thereafter a regularized regression model can estimate the body fat of the user. Once the body fat of the user of determined, the body composition program 420 can track changes in the body fat percentage of the user. FIG. 6A illustrates a baseline forced breath. Specifically graph 601 depicts the flow rate with respect to volume of a normal forced breath 620.

The flow rate of the forced breath 620 peaks at the PEF 610A and then slows until FVC 635A, similar to FVC 520 of FIG. 5. Line 630 indicates the one second time mark for the $FEV_1$, similar to $FEV_1$ 528 of FIG. 5. The slope and shape of the forced breath 620 can analyze the level of obstruction of the forced breath.

FIG. 6B illustrates a graph 602 depicting a single forced breath a user took. Specifically, FIG. 6B illustrates an obstructed forced breath. Specifically graph 602 depicts the flow rate with respect to volume of a forced breath 622 that is slightly obstructed due to excess visceral fat. The flow rate of the forced breath 622 peaks at the PEF 610A and then slows until FVC 635A, similar to FVC 520 of FIG. 5. Line 630 indicates the one second time mark for the $FEV_1$, similar to $FEV_1$ 528 of FIG. 5. The slope and shape of the forced breath 622 can be compared to the slope and shape of the forced breath 620. Forced breath 622 has a steeper slope as compared to the forced breath 620, indicating an intensity of an obstruction.

FIG. 6C illustrates a graph 603 depicting a single forced breath a user took. Specifically, FIG. 6C illustrates a restricted forced breath. Specifically graph 602 depicts the flow rate with respect to volume of a forced breath 624 that is severely restricted due to a significant excess visceral fat. The flow rate of the forced breath 624 peaks at the PEF 610B, as compared to the forced breath of PEF 610A, of FIGS. 6A and 6B. Similarly, the flow rate of the forced breath 624 slows until FVC 635B, as compared to the forced breath of FVC 635A, of FIGS. 6A and 6B. Line 630 indicates the one second time mark for the $FEV_1$, similar to $FEV_1$ 528 of FIG. 5. The slope and shape of the forced breath 624 can be compared to the slope and shape of the forced breath 620 and 622. Forced breath 624 has is significantly more rounded and has a minimal slope as compared to the forced breath 620 and 622, indicating a restriction.

FIG. 6D is provided to compare all three forced breaths 620, 622, and 624 on a singular graph 650. In certain embodiments, body composition program 420 can use the forced breath 620 as a base line. Thereafter for each future received forced breath the body composition program 420 can compares the newly received forced breath to the forced breath 620. In certain embodiments, body composition program 420 can display on display 414, multiple forced breathes, similar to FIG. 6D in order to provide a visual comparison of multiple forced breaths of the user. By displaying multiple forced breaths for the user to view, provides a visual indication the user as to whether the forced breath appears to be improving or degrading based on the shape of the forced breath do to an increase or loss of visceral fat.

Figure 7:
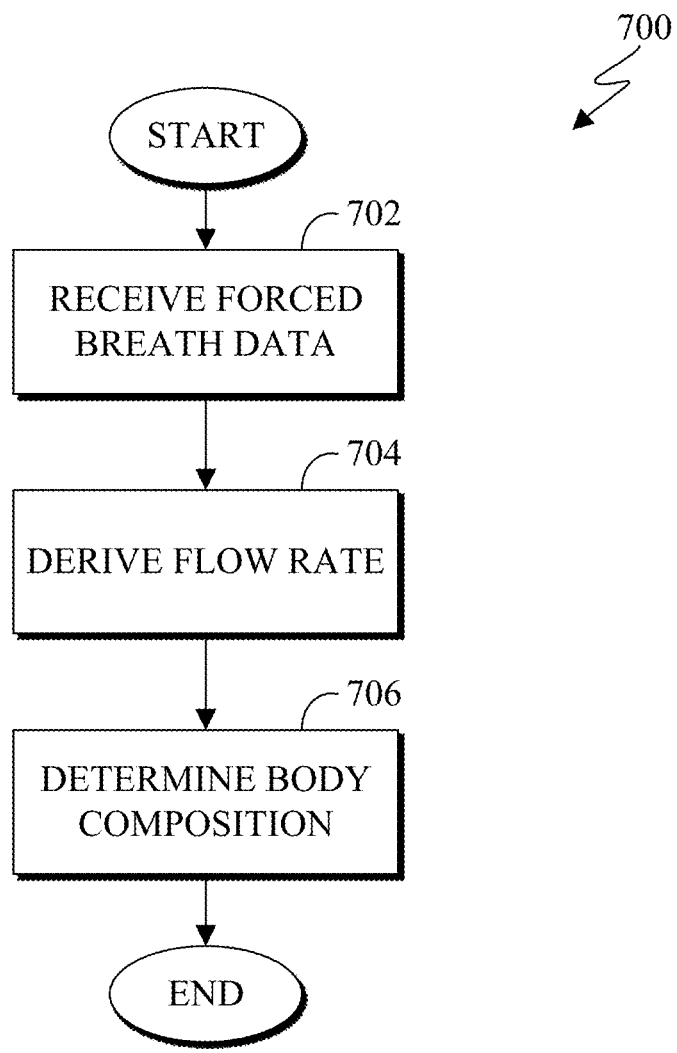
FIG. 7 illustrates a method for estimating body composition in accordance with an embodiment of this disclosure.

FIG. 7 illustrates a method for estimating body composition in accordance with an embodiment of this disclosure. FIG. 7 does not limit the scope of this disclosure to any particular embodiments. While process 700 depicts a series of sequential steps, unless explicitly stated, no inference should be drawn from that sequence regarding specific order of performance, performance of steps or portions thereof serially rather than concurrently or in an overlapping manner, or performance of the steps depicted exclusively without the occurrence of intervening or intermediate steps. For ease of explanation, the method of estimating body composition described with respect to the server 200 of FIG. 2, the electronic device 300 of FIG. 3 and electronic device 410 of FIG. 4. However, the process 700 can be used with any other suitable system.

In block 702, the body composition program 420 receives forced breath data from receiver 416. In certain embodiments, the received forced breath data is captured by a microphone. In certain embodiments, the received forced breath data is captured by a radar detector. In certain embodiments, the received forced breath data is captured by a microphone associated with a mobile device (similar to mobile device 108 of FIG. 1) and transmitted through the telecommunication system to a server for processing, similar to a call in service. In certain embodiments, the received forced breath data is accompanied by a SpO2 reading of the user while performing the forced breath. In certain embodiments, the received forced breath data is accompanied with personal user data. Personal user data can include habit data, such as physical activity level, stress levels, weight, height, gender, food intake, water intake, amount of caffeine, quantity of sleep, quality of sleep and the like of the user. In certain embodiments, the received forced breath data also includes the BIA of the user.

In block 704, the body composition program 420 derives the various flow rate parameters from the forced breath received in block 702. For example, the body composition program 420 derives various parameters associated with the forced breath such as the FVC 520, the ERV 534, the $FEV_1$ 528, the ratio of $FEV_1$ 528 to the FVC 520, and the PEF. In certain embodiments, the body composition program 420 and the flow rate module are a singular element and then the body composition program 420 derives the parameters associated with the forced breath. In certain embodiments, the body composition program 420 and the flow rate module 418 are separate elements and the flow rate module 418 derives the parameters associated with the forced breath.

In block 706, the body composition program 420 analyzes the parameters derived from the received forced breath and determines the body composition in relation to the visceral fat of the user. The body composition program 420 synthesizes the parameters with any additional received data such as the SpO2 reading of the user while performing the forced breath, personal user data, and the BIA of the user. In certain embodiments, the weight of the user is factored in to the determination of the body composition of the user. For example, the weight of the user can be used as a multiplier factor affecting each parameter of the forced breath and the additional received data. In certain embodiments, the body composition program 420 identifies a breathing disorder of the individual, based on the parameters associated with the forced breath. In certain embodiments, body composition program can identify a breathing disorder based on the received SpO2 data. The SpO2 data can indicate a breathing disorder such as COPD, Asthma, and a variety of other lung diseases. For example, individuals that have COPD often have a low SpO2 level as compared to a healthy individual. When a breathing disorder of the individual is identified, the body composition program 420 can adjust the parameters to account for the breathing disorder to determine the body composition of the user. For example, if the parameter of FVC 520 is not within the range associated with a particular age and gender of the user, the body composition program 420 can identify a particular breathing disorder and adjust the body composition analysis to determine an accurate body composition of visceral fat of the user.

In certain embodiments, the body composition program 420 can provide guidance to a user in order to receive an accurate forced breath for analysis. For example, the body composition program 420 can display an image of an ideal forced breath graph, similar to FIG. 6A. The body composition program 420 can then instruct the user to perform a forced breath. While the user is performing the forced breath, the body composition program 420 can indicate how close the user is to the display an image of the ideal forced breath graph. In another example, the body composition program 420 can display an image of a previous forced breath graph, similar to FIG. 5 or FIG. 6. While the user is performing the forced breath, the body composition program 420 can indicate if the forced breath currently received, is an improved reading of the previous forced breath.

In certain embodiments, the body composition program 420 can track the measured body composition of the user. Upon detecting a change in an aspect of the body composition, the body composition program 420 can alert the user. For example, the alert can include a notification that the user is improving. In another example, the alert can include a notification suggesting lifestyle improvements to the user, such as increasing the activity level of the user, eating less, adopting a healthier life style, and the like.

In certain embodiments, the body composition program 420 is a call in service. For example, a user calls a specific number, and is promoted to perform a forced breath into the microphone of the phone. The forced breath data of the individual is transmitted over the telecommunication network as a voice call to a receiver that is a computing device (similar to server 104 of FIG. 1 and server 200 of FIG. 2) that includes the body composition program 420. The body composition program 420 then synthesize the audio data and extracts the various forced breathing parameters. Thereafter, the body composition program 420 estimates the body fat of the user based on a regression model. The call in server can prompt the user for basic biological information such as the age, gender, and weight of the individual. If the call in server prompts the user for basic biological information, then the body composition program 420 estimates the body fat of the user based on a regression model that is tailored and personalized to the individual. The body composition program 420 can then email or send an SMS message of the results to the user.

In certain embodiments, the body composition program 420 can receive BIA data. The BIA data can be received from the wrist of the user. For example, the user can wear a wrist band that includes electrodes for detecting the impedance of the user. In certain embodiments, the derived BIA of the user is limited to the upper body resistance of the user. The body composition program 420 can complement the derived forced breathing parameters with the BIA measurements in order to determine a more accurate body composition.

In certain embodiments, the body composition program 420 requires only a mobile device, similar to mobile device 108 of FIG. 1, electronic device 300 of FIG. 3 and electronic device 410 of FIG. 4 to determine the body composition of the user. For example, additional equipment or devices are not necessary to capture a forced breath and determining the various parameters associated therewith. In certain embodiments, additional equipment or devices are utilized to increase the accuracy of the body composition analysis. For example, a BIA device can be used to increase the accuracy of the body composition analysis.

Although the figures illustrate different examples of user equipment, various changes may be made to the figures. For example, the user equipment can include any number of each component in any suitable arrangement. In general, the figures do not limit the scope of this disclosure to any particular configuration(s). Moreover, while figures illustrate operational environments in which various user equipment features disclosed in this patent document can be used, these features can be used in any other suitable system.

None of the description in this application should be read as implying that any particular element, step, or function is an essential element that must be included in the claim scope. The scope of patented subject matter is defined only by the claims. Moreover, none of the claims is intended to invoke 35 U.S.C. § 112(f) unless the exact words "means for" are followed by a participle. Use of any other term, including without limitation "mechanism," "module," "device," "unit," "component," "element," "member," "apparatus," "machine," "system," "processor," or "controller," within a claim is understood by the applicants to refer to structures known to those skilled in the relevant art and is not intended to invoke 35 U.S.C. § 112(f).

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. A method for determining body composition, the method comprising:
   receiving sound representing a set of forced breath data from an electronic device;
   deriving a flow rate based on the sound representing the set of forced breath data; and
   determining a body composition based on the derived flow rate of the set of forced breath data.

2. The method of claim 1, further comprising receiving a radar signal, representing the set of forced breath data, from a radar detector, wherein the flow rate is based on the radar signal.

3. The method of claim 1, further comprising receiving, from a telecommunication network the sound representing the set of forced breath data.

4. The method of claim 1, further comprising:
   receiving a body impedance measurement;
   deriving a body impedance analysis based on the received body impedance measurement; and
   determining the body composition based on the flow rate and the body impedance analysis.

5. The method of claim 1, further comprising:
   receiving, from an SpO2 sensor, a set of SpO2 data associated with the electronic device while receiving the set of forced breath data;
   deriving a blood oxygenation level based on the received set of SpO2 data; and
   determining the body composition based on the flow rate and the blood oxygenation level.

6. The method of claim 5, further comprising:
   determining a breathing disorder based on the received set of SpO2 data;
   adjusting a set of parameters associated with the derived flow rate, based on the breathing disorder; and
   determining the body composition based on the flow rate and the adjusted set of parameters.

7. The method of claim 1, further comprising:
   receiving a plurality of demographic factors; and
   adjusting a set of parameters associated with the derived flow rate, based on the plurality of demographic factors.

8. An electronic device comprising:
   a communication interface;
   a memory; and
   at least one processor coupled to the communication interface and the memory, the at least one processor is configured to:
      receive sound representing a set of forced breath data from the communication interface;
      derive a flow rate based on the sound representing the set of forced breath data; and
      determine a body composition based on the derived flow rate of the set of forced breath data.

9. The electronic device of claim 8, wherein the at least one processor is further configured to receive a radar signal, representing the set of forced breath data, from a radar detector, wherein the flow rate is based on the radar signal.

10. The electronic device of claim 8, wherein the at least one processor is further configured to receive from a telecommunication network, the sound representing the set of forced breath data.

11. The electronic device of claim 8, wherein the at least one processor is further configured to:
   receive a body impedance measurement;
   derive a body impedance analysis based on the received body impedance measurement; and
   to determine the body composition based on the flow rate and the body impedance analysis.

12. The electronic device of claim 8, wherein the at least one processor is further configured to:
   receive, from an SpO2 sensor, a set of SpO2 data associated with the electronic device while receiving the set of forced breath data;

derive a blood oxygenation level based on the received set of SpO2 data; and
determine the body composition based on the flow rate and the blood oxygenation level.

13. The electronic device of claim 12, wherein the at least one processor is further configured to:
determine a breathing disorder based on the received set of SpO2 data;
adjust a set of parameters associated with the derived flow rate, based on the breathing disorder; and
determine the body composition based on the flow rate and the adjusted set of parameters.

14. The electronic device of claim 8, wherein the at least one processor is further configured to:
receive a plurality of demographic factors; and
adjust a set of parameters associated with the derived flow rate, based on the plurality of demographic factors.

15. A non-transitory computer readable medium embodying a computer program, the computer program comprising computer readable program code that, when executed by at least one processor of an electronic device, causes the at least one processor to:
receive sound representing a set of forced breath data from the electronic device;
derive a flow rate based on the sound representing the set of forced breath data; and
determine a body composition based on the derived flow rate of the set of forced breath data.

16. The non-transitory computer readable medium of claim 15, further comprising program code that when executed by the at least one processor of the electronic device, causes the at least one processor to:
receive a radar signal, representing the set of forced breath data, from a radar detector, wherein the flow rate is based on the radar signal.

17. The non-transitory computer readable medium of claim 15, further comprising program code that when executed by the at least one processor of the electronic device, causes the at least one processor to:
receive, from a telecommunication network the sound representing the set of forced breath data.

18. The non-transitory computer readable medium of claim 15, further comprising program code that when executed by the at least one processor of the electronic device, causes the at least one processor to:
receive, from an SpO2 sensor, a set of SpO2 data associated with the electronic device while receiving the set of forced breath data;
derive a blood oxygenation level based on the received set of SpO2 data; and
determine the body composition based on the flow rate and the blood oxygenation level.

19. The non-transitory computer readable medium of claim 18, further comprising program code that when executed by the at least one processor of the electronic device, causes the at least one processor to:
determine a breathing disorder based on the received set of SpO2 data;
adjust a set of parameters associated with the derived flow rate, based on the breathing disorder; and
determine the body composition based on the flow rate and the adjusted set of parameters.

20. The non-transitory computer readable medium of claim 15, further comprising program code that when executed by the at least one processor of the electronic device, causes the at least one processor to:
receive a plurality of demographic factors; and
adjust a set of parameters associated with the derived flow rate, based on the plurality of demographic factors.

* * * * *